United States Patent [19]

Bedeschi et al.

[11] Patent Number: 5,602,141

[45] Date of Patent: Feb. 11, 1997

[54] CAMPTOTHECIN DERIVATIVES AND PROCESS FOR THEIR PREPARATION

[75] Inventors: Angelo Bedeschi, Milan; Franco Zarini, Settimo Milanese; Walter Cabri, Rozzano; Ilaria Candiani, Busto Arsizio; Sergio Penco; Laura Capolongo, both of Milan, all of Italy

[73] Assignee: Pharmacia & Upjohn S.P.A., Milan, Italy

[21] Appl. No.: 389,190

[22] Filed: Feb. 15, 1995

[30] Foreign Application Priority Data

Feb. 16, 1994 [GB] United Kingdom .................. 9402934

[51] Int. Cl.$^6$ ...................... A61K 31/47; C07D 491/22
[52] U.S. Cl. .................. 514/279; 514/233.2; 514/253; 514/283; 544/125; 544/361; 546/41; 546/48
[58] Field of Search ................... 514/283, 279; 546/48, 41

[56] References Cited

U.S. PATENT DOCUMENTS

| | | | |
|---|---|---|---|
| 4,399,276 | 8/1983 | Miyasaka | 546/48 |
| 4,943,579 | 7/1990 | Vishnuvajjala et al. | 546/48 |
| 4,981,968 | 1/1991 | Wall et al. | 546/48 |
| 5,162,532 | 11/1992 | Comins | 546/48 |
| 5,180,722 | 1/1993 | Wall | 546/48 |
| 5,227,380 | 7/1993 | Wall et al. | 546/48 |
| 5,401,747 | 5/1995 | Wall et al. | 546/48 |

FOREIGN PATENT DOCUMENTS

| | | |
|---|---|---|
| 0321122 | 6/1989 | European Pat. Off. . |
| 0325247 | 7/1989 | European Pat. Off. . |
| 0418099 | 3/1991 | European Pat. Off. . |
| WO91/04260 | 4/1991 | WIPO . |
| WO92/05785 | 4/1992 | WIPO . |

OTHER PUBLICATIONS

Journal of Medicinal Chemistry, vol. 34, No. 1, pp. 98–107, Jan. 1991, W. D. Kingsbury, et al., "Synthesis of Water–Soluble (Aminoalkyl) Camptothecin Analogues: Inhibition of Topoisomerase I and Antitumor Activity".

Journal of Medicinal Chemistry, vol. 36, No. 18, pp. 2689–2700, Sep. 3, 1991, M. E. Wall, et al., "Plant Antitumor Agents. 30. Synthesis and Structure Activity of Novel Camptothecin Analogs".

Cancer Research, vol. 49, No. 6, pp. 1465–1469, Mar. 15, 1989, C. Jaxel, et al., "Structure–Activity Study of the Actions of Camptothecin Derivatives on Mammalian Topoisomerase I: Evidence for a Specific Receptor Site and a Relation to Antitumor Activity".

Cancer Research, vol. 49, No. 16, pp. 4385–4389, Aug. 15, 1989, Yaw–Huei Hsiang, et al., "DNA Topoisomerase I–Mediated DNA Cleavage and Cytotoxicity of Camptothecin Analogues".

Chemical & Pharmaceutical Bulletin, vol. 39, No. 12, pp. 3183–3188, Dec. 1991, S. Sawada, et al., "Synthesis and Antitumor Activity of 20(S)–Camptothecin Derivatives: A–Ring Modified and 7,10–Disubstituted Camptothecins".

J. Med. Chem., vol. 30, No. 10, pp. 1774–1779, 1987, M. C. Wani, et al., "Plant Antitumor Agents. 25. Total Synthesis and Antileukemic Activity of Ring A Substituted Camptothecin Analogues. Structure–Activity Correlations".

*Primary Examiner*—Donald G. Daus
*Attorney, Agent, or Firm*—Oblon, Spivak, McClelland, Maier & Neustadt, P.C.

[57] ABSTRACT

The present invention relates to new camptothecin derivatives of the formula (I)

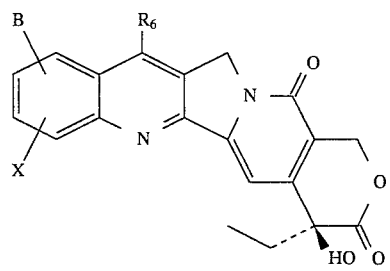

wherein B is a group B' or B"

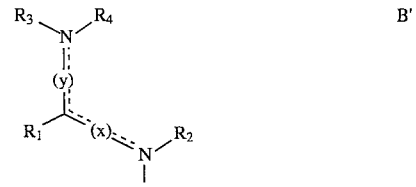

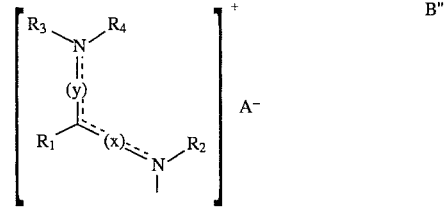

wherein each of (x) and (y) is a single or double bond. The present invention also provides processes for their preparation as well as pharmaceutical compositions containing the same.

6 Claims, No Drawings

CAMPTOTHECIN DERIVATIVES AND PROCESS FOR THEIR PREPARATION

The present invention relates to new camptothecin derivatives, to a process for their preparation, and to pharmaceutical compositions containing them.

BACKGROUND OF THE INVENTION

Camptothecin and some of its analogous compounds such as, for example, 9-amino camptothecin, display potent anti-tumor activity by the inhibition of Topoisomerase I which is a monomeric enzyme involved in some important cellular functions and cellular growth (see, for instance, Wani et al., J. Med. Chem. 1987, 30, 1774; Hsiang et al., Cancer Res. 1989, 49, 4385 and Cancer Res. 1989, 49, 1465).

Unfortunately, camptothecin and some of its derivatives such as the above mentioned 9-amino camptothecin, suffer of low solubility in aqueous solutions. This drawback makes very difficult their administration and the preparation of acceptable pharmaceutical formulations containing them (see, for instance, W. J. Slichenmyer et al., Journal of the National Cancer Institute, Vol. 85, No. 4, 1993, pp 271–291 and, in particular, page 275 for 9-amino camptothecin).

Therefore, there is a need to find new camptothecin derivatives that, while maintaining or increasing biological activity of camptothecin are, in the same time, endowed with water solubility and/or chemicophysical characteristics which make these derivatives suitable for being included in pharmaceutically acceptable formulations.

The compounds of this invention fulfill such a need.

DESCRIPTION OF THE INVENTION

Accordingly, the present invention relates to camptothecin derivatives of formula (I)

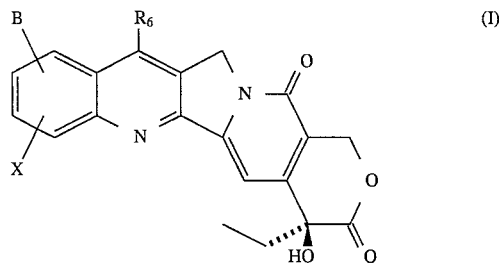

(I)

wherein
B is a group B' or B"

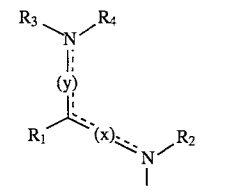

B'

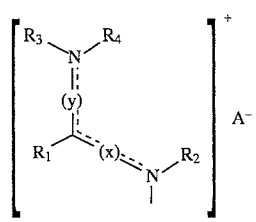

B"

wherein
each of (x) and (y) is a single or double bond, $R_1$ and $R_2$ are each independently hydrogen, $C_1$–$C_6$ alkyl, $C_3$–$C_7$ cycloalkyl, phenyl $C_1$–$C_6$ alkyl or an unsubstituted or substituted phenyl ring, $R_3$ and $R_4$ are
(a) each independently substituents having the same meaning of $R_1$ and $R_2$ or
(b) combined together with the nitrogen atom to which they are linked to form a 3–7 membered saturated, unsubstituted or substituted heteromonocyclic ring, which may additionally contain another heteroatom selected from nitrogen, oxygen and sulphur, and $A^-$ is a pharmaceutically acceptable anion of a pharmaceutically acceptable inorganic or organic acid, provided that
(i) when (x) is a double bond, (y) is a single bond and when (y) is a double bond, (x) is a single bond, and
(ii) when B is a group B', then one of $R_2$, $R_3$ and $R_4$ is absent;

$R_6$ is hydrogen or $C_1$–$C_6$ alkyl; and
X is hydrogen or $C_1$–$C_6$ alkyl; and
X is hydrogen, $C_1$–$C_6$ alkyl, $C_1$–$C_6$ alkoxy, $C_1$–$C_6$ acyloxy, $C_3$–$C_7$ cycloalkyl, $C_3$–$C_7$ cycloalkoxy, benzoyloxy, amino, hydroxy, nitro, a halogen atom or a methylenedioxy group linked to the positions 10 and 11 of the molecule.

The invention includes also the pharmaceutically acceptable salts of the compounds of formula (I).

In the formulae of the present specification, a dotted line ( . . . ) indicates a substituent in the α-configuration, i.e. below the plane of the ring; a wedged line ( ◢ ) indicates a substituent in the β-configuration, i.e. above the plane of the ring.

In this specification, the hydrocarbon chain of the alkyl, alkoxy and acyloxy groups may be a straight or a branched chain.

Preferably, B is linked to the position 9 or 10 of the molecule.

Preferably, $C_1$–$C_6$ alkyl is methyl, ethyl, n-propyl, isopropyl, n-butyl, isobutyl, sec-butyl or t-butyl.

Preferably, $C_3$–$C_7$ cycloalkyl is cyclopropyl, cyclobutyl, cyclopentyl or cyclohexyl.

Preferably, phenyl $C_1$–$C_6$ alkyl is benzyl, phenyl-ethyl or phenyl-propyl.

Preferably, $C_1$–$C_6$ alkoxy is methoxy, ethoxy, n-propoxy, isopropoxy or n-butoxy.

Preferably, $C_3$–$C_7$ cycloalkoxy is cyclopropoxy, cyclobutoxy, cyclopentyloxy or cyclohexyloxy.

Preferably, $C_1$–$C_6$ acyloxy is acetoxy, propanoyloxy or butanoyloxy.

A halogen atom is chlorine, bromine, fluorine or iodine, preferably chlorine or bromine.

When one of $R_1$, $R_2$, $R_3$ and $R_4$ is an unsubstituted or substituted phenyl ring, it may be represented by a group

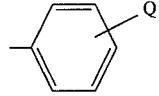

wherein Q is hydrogen, $C_1$–$C_6$ alkyl, $C_1$–$C_6$ alkoxy, $C_1$–$C_6$ acyloxy or a halogen atom.

Preferably, Q is hydrogen; $C_1$–$C_4$ alkyl, in particular methyl, ethyl, n-propyl, isopropyl, n-butyl, isobutyl or sec-butyl; $C_1$–$C_4$ alkoxy, in particular methoxy, ethoxy or isopropoxy; or a halogen atom, in particular chlorine. Particularly preferred values of Q are hydrogen, methyl, ethyl, n-propyl, isopropyl, methoxy and chlorine.

When $R_3$ and $R_4$ combined together with the nitrogen atom to which they are linked form a 3–7 membered saturated, substituted or unsubstituted heteromonocyclic ring, said ring may be represented by a group

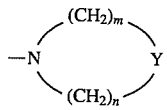

wherein

Y is —O—, —S—, —CH$_2$— or >NR$_5$ wherein R$_5$ is hydrogen, $C_1$–$C_6$ alkyl, or a phenyl ring represented by the above group

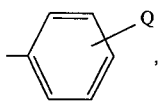

wherein Q is as defined above; and m and n are each independently zero or an integer of 1 to 5, provided that, when one of m and n is zero, the other is not zero and that m+n is not greater than 5.

Preferably, $R_5$ is hydrogen or methyl.

Preferably, $R_3$ and $R_4$ combined together with the nitrogen atom to which they are linked form aziridine, azetidine, pyrrolidine, piperidine, hexamethyleneimine, piperazine, methylpiperazine or morpholine, in particular pyrrolidine, piperidine, hexamethyleneimine, piperazine, methylpiperazine or morpholine.

$A^-$ is a pharmaceutically acceptable anion of pharmaceutically acceptable acids, both inorganic acids such as, e.g., hydrochloric, sulfuric, phosphoric, diphosphoric, hydrobromic or nitric acid, and organic acids such as, e.g., citric, fumaric, maleic, malic, ascorbic, succinic, tartaric, benzoic, acetic, phenylacetic, methanesulfonic, ethanesulfonic, benzenesulfonic or p-toluenesulfonic acid.

Preferably, $A^-$ is a halide, acetate, benzoate, methanesulfonate, or p-toluenesulfonate anion, in particular chloride, acetate, methanesulfonate or p-toluenesulfonate anion.

Preferably, $R_6$ is hydrogen, methyl or ethyl.

Preferably, X is hydrogen, hydroxy, amino, nitro, a halogen atom, methoxy, acetoxy, propanoyloxy, benzoyloxy or 10,11 methylenedioxy, in particular hydrogen, hydroxy, methoxy or 10,11 methylenedioxy.

As already said, the present invention includes camptothecin derivatives of formula (I) in the form of free bases and in the form of pharmaceutically acceptable salts with pharmaceutically acceptable acids both inorganic and organic acids.

Preferred salts according to the invention are the salts with pharmaceutically acceptable acids, both inorganic such as, e.g., hydrochloric, sulfuric, phosphoric, diphosphoric, hydrobromic or nitric acid, and organic acids such as, e.g., citric, fumaric, maleic, malic, ascorbic, succinic, tartaric, benzoic, acetic, phenylacetic, methanesulfonic, ethanesulfonic, benzenesulfonic or p-toluenesulfonic acid.

It is intended that also pharmaceutically acceptable quaternary ammonium salts, namely the compounds of formula (I) wherein B is a group B", are encompassed in the general definition "pharmaceutically acceptable salts" of the compounds of formula (I) of the present invention.

A preferred class of compounds according to the invention are the compounds of formula (I), wherein B is a group B' or B"

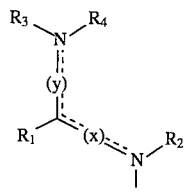

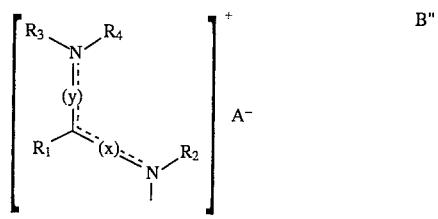

wherein each of (x) and (y) is a single or double bond, $R_1$, $R_2$, $R_3$ and $R_4$ are each independently hydrogen, methyl, ethyl, n-propyl, isopropyl, n-butyl, isobutyl, sec-butyl, t-butyl, cyclobutyl, cyclopentyl, cyclohexyl, benzyl, phenyl-ethyl or an unsubstituted or substituted phenyl ring represented by a group

wherein Q is hydrogen, methyl, ethyl, n-propyl, isopropyl, n-butyl, isobutyl, sec-butyl, methoxy, ethoxy, n-propoxy, isopropoxy, fluorine, chlorine or bromine, $A^-$ is a pharmaceutically acceptable anion of a pharmaceutically acceptable inorganic or organic acid selected from chloride, acetate, methanesulfonate and p-toluenesulfonate, provided that (i) when (x) is a double bond, (y) is a single bond and when (y) is a double bond, (x) is a single bond, and (ii) when B is a grop B', then one of $R_2$, $R_3$ and $R_4$ is absent;

$R_6$ is hydrogen, methyl or ethyl;

X is hydrogen, hydroxy, methoxy or a methylenedioxy group linked to the positions 10 and 11 of the molecule;

and the pharmaceutically acceptable salts thereof.

Another preferred class of compounds according to the invention are compounds of formula (I) wherein B is a group B' or B"

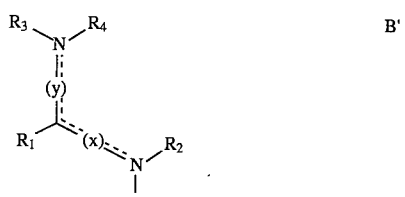

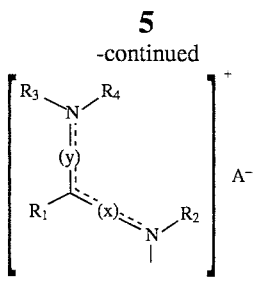

wherein each of (x) and (y) is a single or double bond, $R_1$ and $R_2$ are each independently hydrogen, methyl, ethyl, n-propyl, isopropyl, n-butyl, isobutyl, sec-butyl, t-butyl, cyclobutyl, cyclopentyl, cyclohexyl, benzyl, phenyl-ethyl, or an unsubstituted or substituted phenyl ring represented by a group

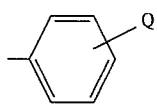

wherein Q is hydrogen, methyl, ethyl, n-propyl, isopropyl, n-butyl, isobutyl, sec-butyl, methoxy, ethoxy, n-propoxy, isopropoxy, fluorine, chlorine or bromine, $R_3$ and $R_4$ combined together with the nitrogen atom to which they are linked form pyrrolidine, piperidine, hexamethyleneimine, piperazine, methylpiperazine or morpholine, $A^-$ is a pharmaceutically acceptable anion of a pharmaceutically acceptable inorganic or organic acid, selected from chloride, acetate, methanesulfonate, and p-toluenesulfonate, provided that (i) when (x) is a double bond, (y) is a single bond and when (y) is a double bond, (x) is a single bond, and (ii) when B is a group B', then one of $R_2$, $R_3$ and $R_4$ is absent;

$R_6$ is hydrogen, methyl or ethyl;

X is hydrogen, hydroxy, methoxy or a methylenedioxy group linked to the positions 10 and 11 of the molecule, and the pharmaceutically acceptable salts thereof.

Examples of specific compounds preferred under the invention are the following:

(1) 9-(iminomethyl-amino)-camptothecin;
(2) 9-(1-imino-ethylamino)-camptothecin;
(3) 9-(methylimino-methylamino)-camptothecin;
(4) 9-(dimethylamino-methyleneamino)-camptothecin;
(5) 9-(dimethylamino-cyclohexyl-methyleneamino)-camptothecin;
(6) 9-[(imino-phenyl-methyl)-amino]-camptothecin;
(7) 9-(1-phenylimino-ethylamino)-camptothecin;
(8) 9-(1-morpholin-4-yl-ethylideneamino)-camptothecin;
(9) 10-(iminomethyl-amino)-camptothecin;
(10) 10-(1-imino-ethylamino)-camptothecin;
(11) 10-(methylimino-methylamino)-camptothecin;
(12) 10-(dimethylamino-methyleneamino)-camptothecin;
(13) 10-(dimethylamino-cyclohexyl-methyleneamino)-camptothecin;
(14) 10-[(imino-phenyl-methyl)-amino]-camptothecin;
(15) 10-(1-phenylimino-ethylamino)-camptothecin;
(16) 10-(1-morpholin-4-yl-ethylideneamino)-camptothecin;
(17) 10-hydroxy-9-(iminomethyl-amino)-camptothecin;
(18) 10-hydroxy-9-(1-imino-ethylamino)-camptothecin;
(19) 10-hydroxy-9-(1-dimethylamino-ethylideneamino)-camptothecin;
(20) 11-hydroxy-9-(iminomethyl-amino)-camptothecin;
(21) 11-hydroxy-9-[(imino-phenyl-methyl)-amino]-camptothecin;
(22) 11-hydroxy-9-(1-phenylimino-ethylamino)-camptothecin;
(23) 10-hydroxy-9-(1-morpholin-4-yl-ethylideneamino)-camptothecin;
(24) 10,11-methylenedioxy-9-(iminomethyl-amino)-camptothecin;
(25) 10,11-methylenedioxy-9-(1-imino-ethylamino)-camptothecin;
(26) 10,11-methylenedioxy-9-[(methylimino-methyl)-amino]-camptothecin;
(27) 10,11-methylenedioxy-9-(1-imino-propylamino)-camptothecin;
(28) 10,11-methylenedioxy-9-(1-methylimino-ethylamino)-camptothecin;
(29) 10,11-methylenedioxy-9-[(ethyl-methyl-amino)-methyleneamino]-camptothecin;
(30) 10,11-methylenedioxy-9-[(cyclohexyl-methyliminomethyl)-amino]-camptothecin;
(31) 9-[1-(4-methyl-piperazin-1-yl)-methyleneamino]-camptothecin;
(32) 10-methoxy-9-(iminomethyl-amino)-camptothecin;
(33) 10-methoxy-9-(1-imino-ethylamino)-camptothecin;
(34) 10-methoxy-9-(1-imino-pentylamino)-camptothecin;
(35) 10-methoxy-9-{[imino-(4-methoxy-phenyl)-methyl]-amino}-camptothecin;
(36) 10-methoxy-9-[(phenylimino-methyl)-amino]-camptothecin;
(37) 10-methoxy-9-(dimethylamino-methyleneamino)-camptothecin;
(38) 10-methoxy-9-(iminomethyl-methylamino)-camptothecin;
(39) 9-(2-methyl-1-imino-propylamino)-camptothecin;
(40) 10-methoxy-9-(2-methyl-1-methylimino-propylamino)-camptothecin;
(41) 10-hydroxy-9-(2,2-dimethyl-1-imino-propylamino)-camptothecin;
(42) 10-methoxy-9-(pyrrolidin-1-yl-methyleneamino)-camptothecin;
(43) 10,11-methylenedioxy-9-[(tert-butylimino-methyl)-amino]-camptothecin;
(44) 9-[(isopropylimino-methyl)-amino]-camptothecin; and
(45) 7-ethyl-9-(iminomethyl-amino)-camptothecin, The structural formula of the above listed compounds is illustrated in the following Table 1, with reference to formula (I)

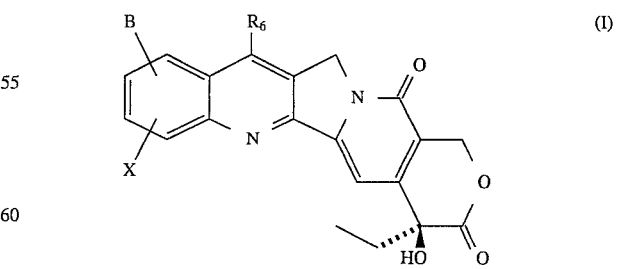

TABLE 1
| COMPOUND | Position of group B | X | $R_1$ | $R_2$ | $R_3$ | $R_4$ | $R_6$ |
|---|---|---|---|---|---|---|---|
| (1) | 9 | H | H | H | H | — | H |
| (2) | 9 | H | —CH$_3$ | H | H | — | H |
| (3) | 9 | H | H | H | —CH$_3$ | — | H |
| (4) | 9 | H | H | — | —CH$_3$ | —CH$_3$ | H |
| (5) | 9 | H | —Cy | — | —CH$_3$ | —CH$_3$ | H |
| (6) | 9 | H | 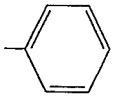 | H | H | — | H |
| (7) | 9 | H | —CH$_3$ | H | 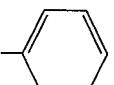 | — | H |
| (8) | 9 | H | —CH$_3$ | — | 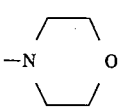 | | H |
| (9) | 10 | H | H | H | H | — | H |
| (10) | 10 | H | —CH$_3$ | H | H | — | H |
| (11) | 10 | H | H | H | —CH$_3$ | — | H |
| (12) | 10 | H | H | — | —CH$_3$ | —CH$_3$ | H |
| (13) | 10 | H | —Cy | — | —CH$_3$ | —CH$_3$ | H |
| (14) | 10 | H |  | H | H | — | H |
| (15) | 10 | H | —CH$_3$ | H |  | — | H |
| (16) | 10 | H | —CH$_3$ | — | 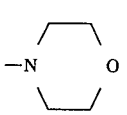 | | H |
| (17) | 9 | 10-OH | H | H | H | — | H |
| (18) | 9 | 10-OH | —CH$_3$ | H | H | — | H |
| (19) | 9 | 10-OH | —CH$_3$ | — | —CH$_3$ | —CH$_3$ | H |
| (20) | 9 | 11-OH | H | H | H | — | H |
| (21) | 9 | 11-OH |  | H | H | — | H |
| (22) | 9 | 11-OH | —CH$_3$ | H |  | — | H |
| (23) | 9 | 10-OH | H | — | 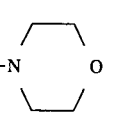 | | H |
| (24) | 9 | 10,11 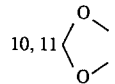 | H | H | H | — | H |
| (25) | 9 | 10,11 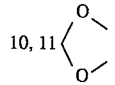 | —CH$_3$ | H | H | — | H |

TABLE 1-continued

| COMPOUND | Position of group B | X | R₁ | R₂ | R₃ | R₄ | R₆ |
|---|---|---|---|---|---|---|---|
| (26) | 9 | 10,11 -O-CH₂-O- (methylenedioxy) | H | H | —CH₃ | — | H |
| (27) | 9 | 10,11 -O-CH₂-CH₂-O- (ethylenedioxy) | Et | H | H | — | H |
| (28) | 9 | 10,11 -O-CH₂-CH₂-O- | —CH₃ | H | —CH₃ | — | H |
| (29) | 9 | 10,11 -O-CH₂-CH₂-O- | H | — | —CH₃ | Et | H |
| (30) | 9 | 10,11 -O-CH₂-CH₂-O- | Cy | H | —CH₃ | — | H |
| (31) | 9 | H | H | — | —N(piperazinyl)N—CH₃ | | H |
| (32) | 9 | 10-OCH₃ | H | H | H | — | H |
| (33) | 9 | 10-OCH₃ | —CH₃ | H | H | — | H |
| (34) | 9 | 10-OCH₃ | n-Bu | H | H | — | H |
| (35) | 9 | 10-OCH₃ | —C₆H₄—OCH₃ (p-methoxyphenyl) | H | H | — | H |
| (36) | 9 | 10-OCH₃ | H | H | —C₆H₅ (phenyl) | — | H |
| (37) | 9 | 10-OCH₃ | H | — | —CH₃ | —CH₃ | H |
| (38) | 9 | 10-OCH₃ | H | —CH₃ | H | — | H |
| (39) | 9 | H | i-Pr | H | H | — | H |
| (40) | 9 | 10-OCH₃ | i-Pr | H | —CH₃ | — | H |
| (41) | 9 | 10-OH | t-Bu | H | H | — | H |
| (42) | 9 | 10-OCH₃ | H | — | —N(piperidinyl) | | H |
| (43) | 9 | 10,11 -O-CH₂-CH₂-O- | H | H | t-Bu | — | H |
| (44) | 9 | H | H | H | i-Pr | — | H |
| (45) | 9 | H | H | H | H | — | Et |

In Table 1, the symbols Et, i-Pr, n-Bu, t-Bu and Cy stand respectively for ethyl, isopropyl, n-butyl, t-butyl and cyclohexyl.

The compounds 1 to 45, listed on the above Table 1, may be also in the form of pharmaceutically acceptable salts.

The compounds of the present invention may be prepared by a process which comprises:

1) reacting a compound of formula (II)

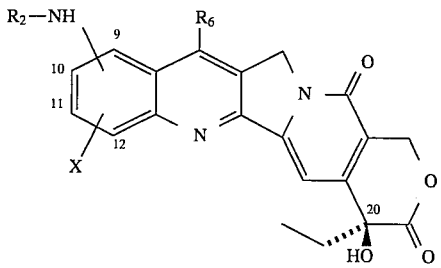

wherein $R_2$, $R_6$ and X are as defined above, with a compound of formula (III)

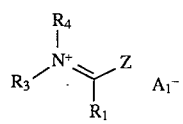

wherein $R_1$, $R_3$ and $R_4$ are as defined above, $A^-_1$ is either a pharmaceutically acceptable anion $A^-$ as defined above or any other suitable anion, and Z is a leaving group, so obtaining a compound of formula (I) wherein $R_6$ and X are as defined above, and wherein, according to the reaction conditions, B is a group B' or B" as defined above; and, if desired, 2) converting a compound of formula (I) wherein $R_6$ and X are as defined above, B is a group B" as defined above wherein one of $R_2$, $R_3$ and $R_4$ is hydrogen, into a corresponding compound of formula (I) wherein $R_6$ and X are as defined above and B is a group B' as defined above, and, if desired, 3) salifying a compound of formula (I) wherein $R_6$ and X are as defined above and B is a group B' as defined above, so obtaining a compound of formula (I) in the form of a pharmaceutically acceptable salt.

The starting compounds of formula (II) have a 20(S)-configuration which is retained throughout the process leading to the compounds of formula (I).

The compounds of formula (II) are typically free of the corresponding 20(R)-isomers.

However, said process may be applied to a racemic mixture of a compound of formula (II) and the corresponding 20(R)-isomer. In that case, a racemic mixture of a compound of formula (I) and a 20(R)-isomer of a compound of formula (I) is obtained.

In the compounds of formula (III), the leaving group Z may be $C_1-C_6$ alkoxy, $C_3-C_7$ cycloalkoxy, $C_1-C_6$ acyloxy, benzoyloxy, $C_3-C_7$ cycloacyloxy, a halogen atom, trifluoromethanesulfonyloxy, p-toluenesulfonyloxy or methanesulfonyloxy.

Preferred meanings which Z may assume include methoxy, ethoxy, propoxy, isopropoxy, acetoxy, propanoyloxy, benzoyloxy, fluorine, chlorine, bromine, iodine, trifluoromethanesulfonyloxy, p-toluenesulfonyloxy or methanesulfonyloxy.

Particularly preferred meanings which Z may assume include methoxy, ethoxy, propoxy, isopropoxy, acetoxy, propanoyloxy, benzoyloxy, chlorine, bromine, trifluoromethanesulfonyloxy, p-toluenesulfonyloxy or methanesulfonyloxy.

In the compound of formula (III) $A^-_1$ is preferably a pharmaceutically acceptable anion $A^-$ as defined above.

The reaction reported under the above item 1) may be performed reacting a compound of formula (II) dissolved in a suitable solvent with from a stoichiometric quantity to a large excess of a compound of formula (III), at a temperature of from about $-20°$ C. to about $100°$ C., preferably from about $0°$ C. to about $80°$ C., for a time which may vary from about few minutes to several days such as from 5 minutes to 3 days, preferably from about one hour to about one day, optionally in the presence of a suitable inorganic or organic base.

When the reaction of item 1) is carried out in the absence of a suitable inorganic or organic base, a compound of formula (I) wherein $R_6$ and X are defined above and wherein B is a group B" as defined above may be obtained. When the reaction of item 1) is carried out in the presence of a suitable inorganic or organic base, a compound of formula (I) wherein $R_6$ and X are as defined above and wherein B is a group B' as defined above may be obtained.

Suitable solvents include dimethylformamide (DMF), water, $CH_3OH$, acetic acid, $CHCl_3$, dioxane, tetrahydrofuran (THF) and mixtures thereof.

Suitable inorganic bases may be, for example, salts with alkali or alkaline earth metals, such as, for example, NaOH, $NaHCO_3$, $Na_2CO_3$ or $CaCO_3$.

Suitable organic bases may be, for example, trialkylamines such as, e.g., triethylamine or diisopropylethylamine amine; or heteroaromatic bases such as, e.g., pyridine or 2,6-$C_1$-$C_6$ alkyl substituted pyridines such as, e.g., 2,6-lutidine.

The conversion reported under the above item 2) may be carried out following conventional procedures; for example, the conversion may be carried out in a suitable aqueous solvent by adding from a stoichiometric amount to a slight excess of an organic or inorganic base.

The organic or inorganic base which can be used under item 2) may be, for example, selected among those optionally used under item 1).

Conventional methods may be used in order to salify a compound of formula (I) as reported under item 3).

In particular, a compound of formula (I) wherein B is a group B' or B" linked to the position 9 of the molecule wherein $R_1$, $R_3$, $R_4$, (x), (y) and $A^-$ are as defined above and $R_2$ is hydrogen, and wherein $R_6$ is as defined above and X is 10- or 12-hydroxy, may be prepared reacting in situ, a corresponding compound of formula (II) wherein $R_6$ is as defined above, $R_2$ is hydrogen and X is 10- or 12-hydroxy, with a compound of formula (III) as defined above, without isolating said compound of formula (II) from the reaction mixture in which it has been obtained, by reduction of a compound of formula (IV)

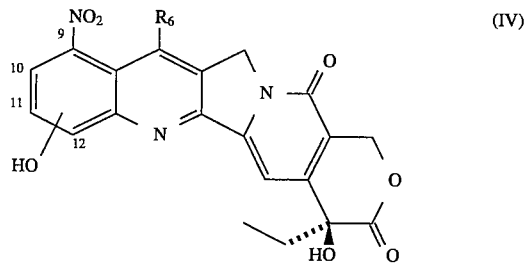

wherein $R_6$ is as defined above and the hydroxy group is linked to the position 10 or 12 of the molecule.

The reduction of the compound of formula (IV) may be carried out, for example, with suitable reducing agents, or by catalytic reduction with suitable catalysts, in the presence of suitable reducing agents. For example, it may be performed as described in: J. March, Advanced Organic Chemistry, Third Edition, 1103. For instance, the reduction may be performed with reducing agents such as, $SnCl_2$, or other metals or metal salts, such as Zn or Fe and their salts, in a suitable solvent such as dilute aqueous HCl, dilute aqueous protic acids, water, ethanol, methanol, or mixtures thereof, at a temperature of from −20° C. to 60° C., for a period of from few minutes to several days such as from 5 minutes to 3 days, for example from 4 hours to 24 hours; or by the use of catalytic amounts of metals which perform nitro group reduction, such as, palladium, platinum oxide, platinum, Pd $L_2$ wherein L is acetate or a halogen atom, rhodium or ruthenium, in the presence of molecular hydrogen or hydrogen sources, such as triethylammonium formate, formic acid, tributyltin hydride, cyclohexadiene, polymethylhydrosiloxane, etc., in a suitable solvent, such as dimethylformamide (DMF), $CH_3OH$, acetic acid, $CHCl_3$, dioxane, or mixtures thereof, at a temperature of from about 0° C. to 100° C., for a time of from 1 hour to 3 days, and at a pressure of from 1 atm to 100 atm.

The compounds of formula (II) and (III) are known compounds or may be obtained following known methods.

The compounds of formula (IV) may be obtained, for example, reacting a 10-hydroxy or 12-hydroxy camptothecin with suitable common nitrating agents such as, e.g., nitric acid, mixtures of nitric and sulphuric acid, or other nitrating agents such as, e.g., potassium nitrate or nitric acid and boron trifluoride such as boron trifluoride monohydrate (see for instance Olah, G. A. et al., Synthesis 1085, 1992), or nitric acid/trifluoromethanesulfonic anhydride (ibid., 1087, 1992), at a temperature of from −20° C. to 100° C., for a time of from a few minutes to several days such as from 5 minutes to 3 days, for example from 4 hours to 24 hours.

The 10-hydroxy and 12-hydroxy camptothecins may be obtained, for example, by known methodologies from camptothecin (see for instance JP-A-59-51288; JP-A-59-51299; J. Med. Chem. 34, 98, 1991; and Chem. Pharm. Bull. 39, 3183, 1991).

In particular, 10-hydroxy-camptothecin is a natural product found in the same plant as camptothecin (see for instance Wani et al., J. Org. Chem., 34, 1364, 1969).

The compounds of formula (I) are water soluble by the virtue of the basic side chain represented by the basic group B which may form salts with pharmaceutically acceptable inorganic or organic acids. The solubility of the compounds of formula (I) in water is especially important since it permits the administration of these compounds in aqueous pharmaceutical compositions.

The compounds of the present invention are endowed with antitumor activity, for example they are effective against leukemia and solid tumors such as, for example, colon and rectal tumors.

The antitumor activity of the compounds of the present invention was shown, for example, by the fact that they have been found to possess both "in vitro" cytotoxic activity and "in vivo" antileukemic activity.

As an example, the activity of 9-(iminomethyl-amino)camptothecin (internal code FCE 28536) and 9-(dimethylamino-methyleneamino)-camptothecin (internal code FCE 29006) were tested according to the following methods (a) and (b).

Method (a): Evaluation of Cytotoxic Activity

L1210 murine leukemia cells were grown in vitro as a stationary suspension in RPMI 1640 medium supplemented with 10% fetal calf serum, 2 mM L-glutamine, 10 µM B-mercaptoethanol, 100 UI/ml penicillin and 100 µg streptomycin. For assaying the cytotoxic activity, exponentialily growing cells were seeded at the concentration of 1×105 cells/ml and exposed to graded doses of the compounds under evaluation for 48 h at 37° C. in an humidified atmosphere of 5% $CO_2$. The number of surviving cells was determined with a Coulter Counter; results are expressed as IC50 (dose causing 50% inhibition of cell growth in treated cultures relative to untreated controls after 48 h treatment).

In this assay, 9-(iminomethyl-amino)-camptothecin (internal code FCE 28536) and 9-(dimethylamino-methyleneamino)-camptothecin (internal code FCE 29006) were tested and the obtained results, which represent the mean of 3 different experiments, are reported on Table 2 below.

TABLE 2

| COMPOUND | $IC_{50}$ (nM) |
|---|---|
| FCE 28536 | 82 |
| FCE 29006 | 120 |

Method (b): Evaluation of Antitumor Activity

L1210 murine leukemia was maintained in DBA2 mice by weekly ip transplants of 105 cells/mouse. For assaying the antileukemic activity, 105 cells/mouse were implanted ip into CD2F1 mice; graded doses of the compounds under evaluation were administered ip 24 h after tumor cells implant on day 1 controls receiving vehicle alone.

The activity of the drugs was determined evaluating the median survival time (MST) of each group of mice.

The obtained results, expressed as % T/C, are reported on Table 3 below.

TABLE 3

| COMPOUND | DOSE (mg/kg) | % T/C |
|---|---|---|
| 28536 | 5 | 150–163 |
|  | 10 | 188 |
|  | 15 | 219–213 |
| 29006 | 5 | 150 |
|  | 10 | 163 |
|  | 15 | 175 |

% TC = MST treated mice/MST contol mice × 100

A human or animal body may thus be treated by a method which comprises the administration thereto of a pharmaceutically effective amount of a compound of formula (I) or salt thereof.

The condition of the human or animal can thereby be improved.

The compounds of the invention can be administered in a variety of dosage forms, e.g. orally, in the form of tablets, capsules, lozengers, liquid solutions or suspensions; rectally, in the form of suppositories; parenterally, e.g. intramuscularly, intravenously, intradermally or subcutaneously; or topically.

The dosage depends upon, for example, the camptothecin derivative employed, the potency of the camptothecin derivative, the age, weight, condition of the patient and administration route; specific dosage regimens may be fit to any particular subject on the basis of the individual need and the professional judgement of the person administering or supervising the administration of the aforesaid compounds. For example, the dosage adopted for the administration to adult humans may range from 0.1 to 60 mg of camptothecin derivative per kg of body weight; a particularly preferred range may be from 1 to 40 mg of camptothecin derivative per kg of body weight.

The dosages may be administered at once or may be divided into a number of smaller doses to be administered at varying intervals of time. Pharmaceutical compositions containing as an active ingredient a compound of formula (I) or a pharmaceutically acceptable salt thereof in association with a pharmaceutically acceptable carrier and/or diluent are also within the scope of the present invention.

These pharmaceutical compositions contain an amount of active ingredient which is therapeutically effective to display antileukemic and/or antitumor activity.

There may also be included as a part of the pharmaceutical compositions according to the invention, pharmaceutically acceptable binding agents and/or adjuvant materials. The active ingredients may also be mixed with other active principles which do not impair the desired action and/or supplement the desired action. The pharmaceutical compositions containing the compounds of the invention are usually prepared following conventional methods and may be administered in a pharmaceutically suitable form.

For example, the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, microcrystalline cellulose, carboxymethylcellulose or polyvinyl pyrrolidone; diaggregating agents, e.g. a starch, alginic acid, alginates or sodium starch glycolate; effervescing mixtures; dyestuffs; sweetening agents, e.g. sucrose or saccharin; flavouring agents, e.g. peppermint, methylsalicylate or orange flavouring; wetting agents, such as lecithin, polysorbates, laurylsulphates; and, in general, non-toxic and pharmacologically inactive substances used in pharmaceutical formulations.

When the dosage unit form is a capsule, it may contain, in addition to material of the above type, a liquid carrier such as, e.g., a fatty oil.

Said pharmaceutical preparations may be manufactured in known manner, for example, by means of mixing, granulating, tabletting, sugar-coating or film-coating processes. The liquid dispersions for oral administration may be, e.g. syrups, emulsions and suspensions. The syrups may contain as carrier, for example, saccharose or saccharose with glycerine and/or mannitol and/or sorbitol; in particular, a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusions may contain as carrier, for example, sterile water, or preferably they may be in the form of sterile, aqueous, isotonic saline solutions.

The solutions or suspensions for parenteral therapeutic administration may also contain antibacterial agents, such as benzyl alcohol or methyl parabens; antioxidants, such as ascorbic acid or sodium bisulphite; chelating agents, such as ethylenediaminetetraacetic acid; buffers, such as acetates, citrates or phosphates and agents for the adjustment of tonicity, such as sodium chloride or dextrose. The parenteral preparation can be enclosed in ampoules, disposable syringes or multiple dose vials made of glass or plastic.

The suppositories may contain together with the active compound a pharmaceutically acceptable carrier, e.g., cocabutter, polyethylene glycol, a polyoxyethylene sorbitan fatty acid ester surfactant or lecithin.

Compositions for topical application, such as, e.g., creams, lotions or pastes, may be, e.g., prepared by admixing the active ingredient with a conventional oleaginous or emulsifying excipient.

The following examples illustrate but do not limit the invention.

The number into bracket reported after the chemical name of the compounds prepared according to the following examples corresponds to the number given to the preferred compounds listed on pages 11, 12 and 13 of the present specification.

EXAMPLE 1

9-(iminomethyl-amino)-camptothecin (1)

To a stirred solution of 9-amino camptothecin (0.5 g) in DMF (100 ml), ethyl formimidate hydrochloride (2.5 g) was added at room temperature, and the resulting mixture was stirred overnight. The solid was filtered off and the filtrate was evaporated in vacuo. The residue was taken-up with water and the pH of the resulting solution was adjusted to about 6.5. The precipitated solid was collected by filtration, carefully washed with small portions of cold water, and then dried to yield the title product (0.25 g).

$^1$NMR (DMSO-$d_6$), δppm: 0.87 (3H, t, J=7.3 Hz); 1.85 (2H, m); 5.27 (2H, s); 5.41 (2H, s); 6.50 (1H, broad signal); 7.04 (1H, d, J=7.3 Hz); 7.10 (2H, broad signal); 7.31 (1H, s); 7.67 (1H, dd, J=7.3, 8.5 Hz); 7.73 (1H, d, J=8.5 Hz); 7.79 (1H, m); 8.94 (1H, s). MS (FD): 390.

The title product (0.1 g) was suspended in water (2 ml) and 1N HCl (0.3 ml) was added. The resulting yellow solution was then freeze dries to yield the hydrochloride salt of the title product.

Following analogous procedure the below listed compounds and their hydrochloride salts can be prepared:
10,11-methylenedioxy-9-(iminomethyl-amino)-camptothecin (24);
10-methoxy-9-(iminomethyl-amino)-camptothecin (32);
10-(iminomethyl-amino)-camptothecin (9);
11-hydroxy-9-(iminomethyl-amino)-camptothecin (20); and
7-ethyl-9-(iminomethyl-amino)-camptothecin (45).

EXAMPLE 2

10-hydroxy-9-(iminomethyl-amino)-camptothecin (17)

A solution of 10-hydroxy-9-nitro camptothecin (0.5 g) in DMF (100 ml) was hydrogenated at atmospheric pressure and room temperature in the presence of 10% Pd/C (0.05 g) until $H_2$ consumption ceased. The resulting solution was filtered and then treated with ethyl formimidate hydrochloride (1.5 g). The solution was stirred overnight and worked-up as described in Example 1, to yield the title compound (0.1 g).

EXAMPLE 3

9-(1-imino-ethylamino)-camptothecin (2)

To a stirred solution of 9-amino camptothecin (0.5 g) in DMF (100 ml), ethyl acetamidate hydrochloride (2.5 g) was added and the resulting mixture was stirred at 80° C. overnight and worked-up as described in Example 1, to yield the title compound (0.2 g).

Following analogous procedure the below listed compounds and their hydrochloride salts can be prepared:
10,11-methylenedioxyoxy-9-(1-imino-ethylamino)-camptothecin (25);
10-methoxy-9-(1-imino-methylamino)-camptothecin (38);
10-methoxy-9-(1-imino-ethylamino)-camptothecin (33);
10-(1-imino-ethylamino)-camptothecin (10);
9-[(imino-phenyl-methyl)-amino]-camptothecin (6);
10-[(imino-phenyl-methyl)-amino]-camPtothetin (14);
11-hydroxy-9-[(imino-phenyl-methyl)-amino]-camptothecin (21);
10, 11-methylenedioxy-9-(1-imino-propylamino)-camptothecin (27);
10-methoxy-9-(1-imino-pentylamino)-camptothecin (34);
10-methoxy-9-{[imino-(4-methoxy-phenyl)-methyl]-amino}-camptothecin (35); and
9-(2-methyl-1-imino-propylamino)-camptothecin (39).

EXAMPLE 4

10-hydroxy-9-(1-imino-ethylamino)-camptothecin (18)

A solution of 10-hydroxy-9-nitro camptothecin (0.5 g) in DMF (100 ml) was hydrogenated at atmospheric pressure and room temperature in the presence of 10% Pd/C (0.1 g) until $H_2$ consumption ceased. The resulting solution was treated with ethyl acetamidate hydrochloride (2.0 g), and left at room temperature overnight. The solution was worked-up as described in previous examples, to yield the title compound (0.2 g).

Following analogous procedure the below listed compounds can be obtained:
10-hydroxy-9-(2,2-dimethyl-1-imino-propylamino)camptothecin (41);
10-hydroxy-9-(1-dimethylamino-ethylideneamino)-camptothecin (19); and
10-hydroxy-9-(1-morpholin-4-yl-ethylideneamino)-camptothecin (23).

EXAMPLE 5

By analogy with the previous Example 1 by using the appropriate imidate, the following compounds can be prepared:
9-(methylimino-methylamino)-camptothecin (3);
9-(dimethylamino-methyleneamino)-camptothecin (4);
9-(dimethylamino-cyclohexyl-methyleneamino)-camptothecin (5);
9-(1-phenylimino-ethylamino)-camptothecin (7);
10-(1-morpholin-4-yl-ethylideneamino)-camptothecin (8);
10-(methylimino-methylamino)-camptothecin (11);
10-(dimethylamino-methyleneamino)-camptothecin (12);
10-(dimethylamino-cyclohexyl-methyleneamino) camptothecin (13);
10-(1-phenylimino-ethylamino)-camptothecin (15);
10-(1-morpholin-4-yl-ethylideneamino)-camptothecin (16);
11-hydroxy-9-(1-phenylimino-ethylamino)-camptothecin (22);
10,11-methylenedioxy-9-[(methylimino-methyl)-amino]-camptothecin (26);
10,11-methylenedioxy-9-(1-methylimino-ethylamino)-camptothecin (28);
10,11-methylenedioxy-9-[(ethyl-methyl-amino)-methylene-amino]-camptothecin (29);
10,11-methylenedioxy-9-[(cyclohexyl-methylimino-methyl)amino]-camptothecin (30);
9-[1-(4-methyl-piperazin-1-yl)-methyleneamino]-camptothecin (31);
10-methoxy-9-[(phenylimino-methyl)-amino]-camptothecin (36);
10-methoxy-9-(dimethylamino-methyleneamino)-camptothecin (37);
10-methoxy-9-(2-methyl-1-methylimino-propylamino)-camptothecin (40);
10-methoxy-9-(pyrrolidin-1-yl-methyleneamino)-camptothecin (42);
10,11-methylenedioxy-9-[(tert-butylimino-methyl)-amino]-camptothecin (43); and
9-[(isopropylimino-methyl)-amino]-camptothecin (44).

EXAMPLE 6

9-(dimethylamino-methyleneamino)-camptothecin (4)

Oxalyl chloride (1.15 ml) in ehter (5 ml) was added at −40° C. to a stirred solution of dimethylformamide (1 ml) in ether (50 ml).

The mixture was then stirred at room temperature for three hours. The precipitate was filtered, washed with ether, and added at room temperature to a solution of 9-amino camptothecin (150 mg) in DMF (20 ml).

The mixture was stirred at room temperature overnight.

The reaction mixture was then evaporated "in vacuo", and the residue was taken up with water. The aqueous solution was then washed twice with $CH_2Cl_2$ and the organic layer was discharged. The pH of the aqueous layer was then adjusted by addition of $NaHCO_3$, till complete precipitation of a yellow-brown solid was observed. The solid was collected by filtration and carefully washed with water. The crude product was then purified with reverse phase chromatography eluting with acidic-water/acetone mixtures. The appropriate fractions were collected, and freeze dried.

The residue was taken-up with water (3 ml), and $NaHCO_3$ was added until a complete precipitation was observed.

The precipitate was collected by filtration, carefully washed with water, and dried, to yield the title product (90 mg).

NMR (DMSO-$d_6$) δ(ppm): 0.87 (3H, T, J=7.3 Hz); 1.85 (2H, m); 3.10 (6H, s); 5.27 (2H, s); 5.41 (2H, s); 6.50 (1H, s); 7.08 (1H, m); 7.31 (1H, s); 7.68 (2H, m); 7.94 (1H, s); 9.04 (1H, s).

MS (FD): 418

The above precipitate (80 mg) was suspended again in water (2 ml) and 1N HCl (0.2 ml) was added. The solution was then freeze-dried to afford the title product as hydrochloride salt.

EXAMPLE 7

9-(1-imino-ethylamino)-camptothecin (2)

The reaction was performed as described in Example 3, but using dimethylacetamide.

After usual work-up there were obtained 0.1 g of the title product.

We claim:

1. A compound of the formula (I)

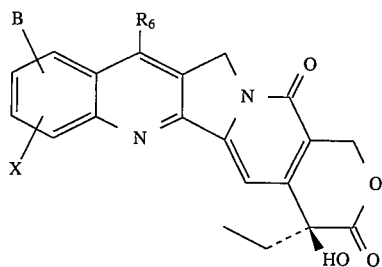

wherein B is a group B' or B"

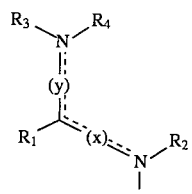

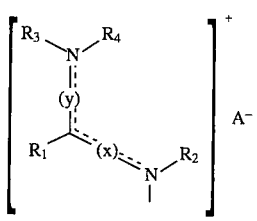

wherein one of (x) and (y) is a single bond and the other is a double bond;

$R_1$, $R_2$, $R_3$ and $R_4$ are each independently hydrogen, $C_1$–$C_6$-alkyl, $C_3$–$C_7$ cycloalkyl, phenyl $C_1$–$C_6$ alkyl or a group of the formula

wherein Q is hydrogen, $C_1$–$C_6$ alkyl, $C_1$–$C_6$ alkoxy, $C_1$–$C_6$ acyloxy or a halogen atom, or $R_3$ and $R_4$ together with the nitrogen atom to which they are linked form a group of the formula

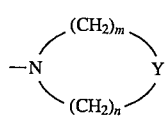

wherein Y is —$CH_2$— and m and n are each independently an integer of 1 to 5 and m+n is not greater than 5; and A is a pharmaceutically acceptable anion of a pharmaceutically acceptable inorganic or organic acid, provided that when B is a group B', then one of $R_2$, $R_3$ and $R_4$ is absent;

$R_6$ is hydrogen or $C_1$–$C_6$ alkyl;

X is hydrogen, $C_1$–$C_6$-alkyl, $C_1$–$C_6$-alkoxy, $C_1$–$C_6$ acyloxy, $C_3$–$C_7$ cycloalkyl, $C_3$–$C_7$ cycloalkoxy, benzoyloxy, hydroxy, nitro, a halogen atom or a methylenedioxy group linked to the position 10 and 11 of the molecule; or a pharmaceutically acceptable salt thereof.

2. The compound according to claim 1, wherein B is B' or B"

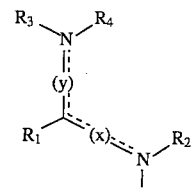

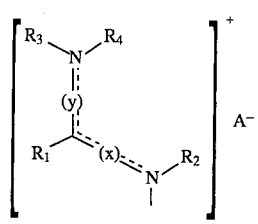

wherein each of (x) and (y) is a single or double bond; $R_1$, $R_2$, $R_3$ and $R_4$ are each independently hydrogen, methyl, ethyl, n-propyl, isopropyl, n-butyl, isobutyl, sec-butyl, t-butyl, cyclobutyl, cyclopentyl, cyclohexyl, benzyl, phenyl-ethyl or a group of the formula

wherein Q is hydrogen, methyl, ethyl, n-propyl, isopropyl, n-butyl, isobutyl, sec-butyl, methoxy, ethyloxy, n-propoxy, isopropoxy, fluorine, chlorine or bromine, A is a pharmaceutically acceptable anion of a pharmaceutically acceptable inorganic or organic acid selected from chloride, acetate, methanesulfonate and p-toluenesulfonate, provided that (i) when (x) is a double bond, (y) is a single bond and when (y) is a double bond, (x) is a single bond, and (ii) when B is B', then one of $R_2$, $R_3$ and $R_4$ is absent;

$R_6$ is hydrogen, methyl or ethyl;

X is hydrogen, hydroxy, methoxy or a methylenedioxy group linked to the positions 10 and 11 of the molecule; or a pharmaceutically acceptable salt thereof.

3. The compound according to claim 1, wherein B is B' or B"

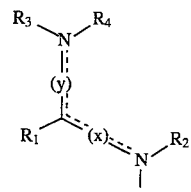

-continued

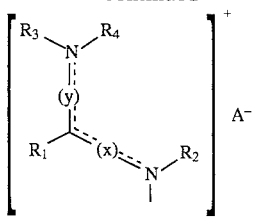

wherein each of (x) and (y) is a single or double bond;

$R_1$ and $R_2$ are each independently hydrogen, methyl, ethyl, n-propyl, isopropyl, n-butyl, isobutyl, sec-butyl, t-butyl, cyclobutyl, cyclopentyl, cyclohexyl, benzyl, phenyl-ethyl, or a group of the formula

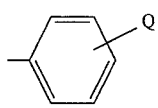

wherein Q is hydrogen, methyl, ethyl, n-propyl, isopropyl, n-butyl, isobutyl, sec-butyl, methoxy, ethyoxy, n-propoxy, isopropoxy, fluorine, chlorine or bromine, $R_3$ and $R_4$ combined together with the nitrogen atom to which they are linked form pyrrolidine, piperidine, hexamethyleneimine, piperazine, methylpiperazine, or morpholine.

4. The compound of claim 1, which is selected from the group consisting of:

(1) 9-(iminomethyl-amino)-camptothecin;
(2) 9-(1-imino-ethylamino)-camptothecin;
(3) 9-(methylimino-methylamino)-camptothecin;
(4) 9-(dimethylamino-methyleneamino)-camptothecin;
(5) 9-(dimethylamino-cyclohexyl-methyleneamino)camptothecin;
(6) 9-[(imino-phenyl-methyl)-amino]-camptothecin;
(7) 9-(1-phenylimino-ethylamino)-camptothecin;
(9) 10-(iminomethyl-amino)-camptothecin;
(10) 10-(1-imino-ethylamino)-camptothecin;
(11) 10-(methylimino-methylamino)-camptothecin;
(12) 10-(dimethylamino-methyleneamino)-camptothecin;
(13) 10-(dimethylamino-cyclohexyl-methyleneamino)camptothecin;
(14) 10-[(imino-phenyl-methyl)-amino]-camptothecin;
(15) 10-(1-phenylimino-ethylamino)-camptothecin;
(17) 10-hydroxy-9-(iminomethyl-amino)-camptothecin;
(18) 10-hydroxy-9-(1-imino-ethylamino)-camptothecin;
(19) 10-hydroxy-9-(1-dimethylamino-ethylidene-amino) camptothecin;
(20) 11-hydroxy-9-(iminomethyl-amino)-camptothecin;
(21) 11-hydroxy-9-[(imino-phenyl-methyl)-amino]-camptothecin;
(22) 11-hydroxy-9-(1-phenylimino-ethylamino)-camptothecin;
(23) 10-hydroxy-9-(1-morpholin-4-yl-ethylidene-amino)camptothecin;
(24) 10,11-methylenedioxy-9-(iminomethyl-amino)camptothecin;
(25) 10,11-methylenedioxy-9-(1-imino-ethylamino)camptothecin;
(26) 10,11-methylenedioxy-9-[(methylimino-methyl)-amino]-camptothecin;
(27) 10,11-methylenedioxy-9-(1-imino-propylamino)camptothecin;
(28) 10,11-methylenedioxy-9-(1-methylimino-ethylamino)camptothecin;
(29) 10,11-methylenedioxy-9-[(ethyl-methyl-amino)methyleneamino]-camptothecin;
(30) 10,11-methylenedioxy-9-[(cyclohexyl-methyliminomethyl)-amino]-camptothecin;
(31) 9-[1-(4-methyl-piperazin-1-yl)-methylene-amino]-camptothecin;
(33) 10-methoxy-9-(1-imino-ethylamino)-camptothecin;
(34) 10-methoxy-9-(1-imino-pentylamino)-camptothecin;
(35) 10-methoxy-9-{[imino-(4-methoxy-phenyl)-methyl]-amino}-camptothecin;
(36) 10-methoxy-9-[(phenylimino-methyl)-amino]-camptothecin;
(37) 10-methoxy-9-(dimethylamino-methyleneamino)-camptothecin;
(38) 10-methoxy-9-(iminomethyl-methylamino)-camptothecin;
(39) 9-(2-methyl-1-imino-propylamino)-camptothecin;
(40) 10-methoxy-9-(2-methyl-1-methylimino-propyl-amino)camptothecin;
(41) 10-hydroxy-9-(2,2-dimethyl-1-imino-propylamino)-camptothecin;
(43) 10,11-methylenedioxy-9-[(tert-butylimino-methyl)-amino]-camptothecin;
(44) 9-[(isopropylimino-methyl)-amino]-camptothecin;
(45) 7-ethyl-9-(iminomethyl-amino)-camptothecin,
and their pharmaceutically acceptable salts.

5. A pharmaceutical composition comprising a suitable carrier and/or diluent and, as an active principle, a compound of the formula (I), as defined in claim 1, or a pharmaceutically acceptable salt thereof.

6. A method of treating leukemia, said method comprising administering a therapeutically effective amount of a compound of formula (I), according to claim 1, or a pharmaceutically acceptable salt thereof, to a patient in need of it.

* * * * *

UNITED STATES PATENT AND TRADEMARK OFFICE
CERTIFICATE OF CORRECTION

PATENT NO. : 5,602,141
DATED : February 11, 1997
INVENTOR(S) : Angelo Bedeschi ET AL It is certified that error appears in the above-identified patent and that said Letters Patent is hereby corrected as shown below:

Column 21, lines 28-29, replace "hexamethyleneimine, piperazine, methylpiperazine, or morpholine" with --or hexamethyleneimine--.

Column 22, lines 5-6, delete "(23) 10-hydroxy-9-(1-morpholin-4-yl-ethylidene-amino)camptothecin;".

Column 22, lines 21-22, delete "(31) 9-[1-(4-methyl-piperazin-1-yl)-methylene-amino]-camptothecin;".

Signed and Sealed this

Twenty-fourth Day of March, 1998

Attest:

BRUCE LEHMAN

*Attesting Officer*    *Commissioner of Patents and Trademarks*